US012648931B2

(12) United States Patent
Dagum

(10) Patent No.: US 12,648,931 B2
(45) Date of Patent: Jun. 9, 2026

(54) COMPOSITIONS, FORMULATIONS, AND METHODS OF TREATING NEURODEGENERATIVE DISEASES

(71) Applicant: Applied Cognition, Inc., Redwood City, CA (US)

(72) Inventor: Paul Dagum, Los Altos Hills, CA (US)

(73) Assignee: Applied Cognition, Inc., Redwood City, CA (US)

( * ) Notice: Subject to any disclaimer, the term of this patent is extended or adjusted under 35 U.S.C. 154(b) by 0 days.

(21) Appl. No.: 19/253,159

(22) Filed: Jun. 27, 2025

(65) Prior Publication Data

US 2026/0000647 A1 Jan. 1, 2026

Related U.S. Application Data

(60) Provisional application No. 63/664,720, filed on Jun. 27, 2024.

(51) Int. Cl.
    *A61K 31/4164* (2006.01)
    *A61K 31/165* (2006.01)

(52) U.S. Cl.
    CPC ........ *A61K 31/4164* (2013.01); *A61K 31/165* (2013.01)

(58) Field of Classification Search
    CPC .......................... A61K 31/4164; A61K 31/165
    See application file for complete search history.

(56) References Cited

U.S. PATENT DOCUMENTS

| | | | |
|---|---|---|---|
| 9,901,650 | B2 | 2/2018 | Nedergaard |
| 11,478,184 | B1 | 10/2022 | Dagum |
| 11,738,022 | B2 * | 8/2023 | Ifantides ............... A61K 31/137 514/249 |
| 11,759,142 | B2 | 9/2023 | Dagum |
| 11,766,576 | B2 | 9/2023 | Jordan |
| 12,004,874 | B2 | 6/2024 | Dagum |
| 12,133,738 | B2 | 11/2024 | Dagum |
| 2010/0029654 | A1 * | 2/2010 | Pasinetti ................ A61K 31/47 |
| 2020/0022919 | A1 | 1/2020 | Dandiker |
| 2020/0297211 | A1 | 9/2020 | Jordan |
| 2020/0338025 | A1 | 10/2020 | Dandiker |
| 2020/0383978 | A1 | 12/2020 | Ifantides |
| 2022/0031663 | A1 | 2/2022 | Nandabalan |
| 2022/0031867 | A1 | 2/2022 | Nedergaard |
| 2022/0072128 | A1 | 3/2022 | Airan |
| 2022/0280423 | A1 | 9/2022 | Nedergaard |
| 2024/0217936 | A1 | 7/2024 | Yang |

FOREIGN PATENT DOCUMENTS

| | | |
|---|---|---|
| KR | 102317379 B1 | 10/2021 |
| KR | 20230087828 A1 | 6/2023 |
| WO | 2018015467 A1 | 1/2018 |
| WO | 2018112269 A1 | 6/2018 |
| WO | WO-2018126182 A1 * | 7/2018 ............. A61K 45/06 |
| WO | 2023073526 A1 | 5/2023 |
| WO | 2023122719 A2 | 6/2023 |
| WO | 2023122720 A1 | 6/2023 |
| WO | 2024023261 A1 | 2/2024 |

OTHER PUBLICATIONS

Dagum, Paul, et al.; A wireless device for continuous measurement of brain parenchymal resistance tracks glymphatic function in humans; Nature Biomedical Engineering; May 27, 2025; https://doi.org/10.1038/s41551-025-01394-9.
Persson, Niklas Daniel Ake, et al.; Could dexmedetomidine be repurposed as a glymphatic enhancer?; Trends in Pharmacological Sciences; Dec. 2022; pp. 1030-1040; vol. 43, No. 12.
U.S. Food and Drug Administration; Prescribing Label For Dexmedetomidine Hydrochloride; Reference ID: 3836249; https://www.fda.gov/drugsatfda.
Li, Xin, et al.; Design, Synthesis, and Bioevaluation of Dexmedetomidine Prodrug; ACS Medicinal Chemistry Letters; Mar. 6, 2023; pp. 405-410; vol. 14.
Lombardo, et al., "Treatment of Acute Delirium in a Patient with Parkinson's Disease by Transfer to the Intensive Care Unit and Administration of Dexmedetomidine", J. of Movement Disorder, 2020, 13(2): 159-162.
International Search Report and Written Opinion in PCT App. No. PCT/US2025/035741 dated Sep. 17, 2025.
Wang, Jun, et al., Valsartan lowers brain β-amyloid protein levels and improves spatial learning in a mouse model of Alzheimer disease, The Journal of Clinical Investigation, Nov. 2007, pp. 3393-3402, vol. 17(11).
Karczewski, Peter, et al., Role of alpha1-adrenergic receptor antibodies in Alzheimer's disease, Frontiers in Bioscience, Jun. 1, 2018, 23, pp. 2082-2089.

* cited by examiner

*Primary Examiner* — Kevin E Weddington
(74) *Attorney, Agent, or Firm* — King & Spalding LLP

(57) ABSTRACT

The present disclosure relates to compositions, formulations, and associated methods for treating neurodegenerative diseases, wherein the compositions include an alpha-1 adrenergic agonist, such as midodrine, and an alpha-2A adrenergic agonist, such as dexmedetomidine. Upon administering to a human subject, the alpha-2A adrenergic agonist crosses the subject's blood-brain barrier thereby acting upon the subject's central nervous system, whereas the alpha-1 adrenergic agonist does not cross the subject's blood-brain barrier. The alpha-1 adrenergic agonist minimizes or eliminates the systemic vascular effects induced by the alpha-2A adrenergic agonist that causes the negative cerebral autoregulatory response, thereby enabling the alpha-2A adrenergic agonist to increase glymphatic flow in the subject's brain.

30 Claims, 7 Drawing Sheets

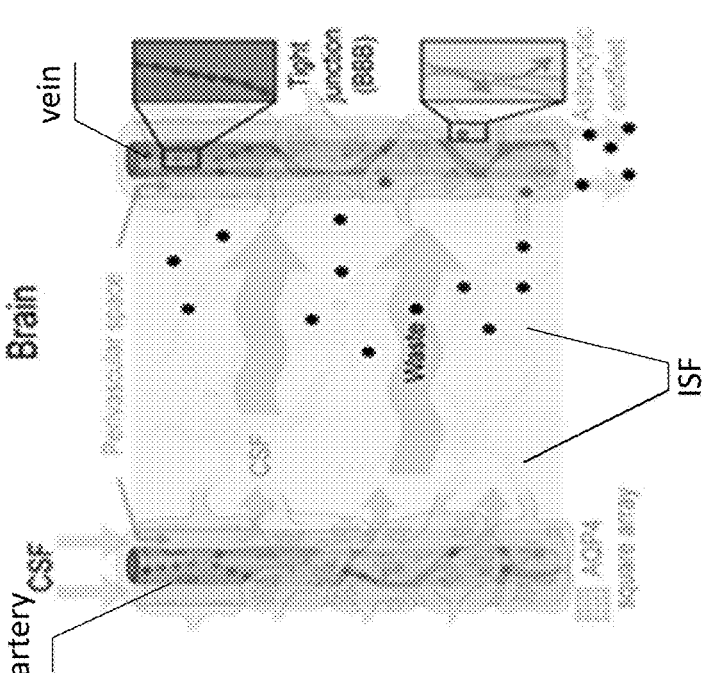

$$Glymphatic\ Flow = \frac{\Delta Pressure}{R}$$

- From our dynamic impedance measurements we derive changes in total brain interstitial and intracellular compartment volumes

- An increase in interstitial volume and decrease in intracellular volume reduces the flow resistance R within the brain tissue and thereby increases glymphatic flow Compartment Volumes

FIG. 2

Study 1

FIG. 3

Study 2

FIG. 4

The required dose of midodrine at a new dexmedetomidine dose can be determined by analyzing blood pressure response curves shown below (1) Wright, R. A., et al. "A double-blind, dose-response study of midodrine in neurogenic orthostatic hypotension." *Neurology* 51.1 (1998): 120-124.

COMPOSITIONS, FORMULATIONS, AND METHODS OF TREATING NEURODEGENERATIVE DISEASES

RELATED APPLICATIONS

The present application claims the benefit of U.S. Provisional Patent Application No. 63/664,720, filed Jun. 27, 2024, the entire content of which is incorporated herein by reference.

TECHNICAL FIELD

The disclosure relates generally to compositions, formulations, and associated methods for treating neurodegenerative diseases, wherein the compositions include an alpha-1 adrenergic agonist, such as midodrine, and an alpha-2A adrenergic agonist, such as dexmedetomidine.

BACKGROUND

Interest in brain fluid transport systems has risen rapidly in recent years with the discovery of the glymphatic system and its role in brain protein clearance involved in neurodegeneration such as amyloid-β, tau, alpha-synuclein and TDP-43. Inhibition of glymphatic flow accelerates pathological protein accumulation accelerating neurodegeneration in animal models of Alzheimer's disease, traumatic brain injury, Parkinson's disease, Frontal Temporal Dementia and other neurodegenerative disorders. The glymphatic flow is primarily active during sleep, particularly NREM sleep, and driven by cerebrovascular arterial pulsations and widening of the brain parenchymal interstitial spaces. Thus, sleep, cerebrovascular integrity and reduced brain parenchymal flow resistance are required for clearance of waste products that build up in the awake brain. A reduction in glymphatic flow results in accumulation of protein in the brain that leads to neurodegeneration (disorders known as neurodegenerative proteinopathies) and which can be detected with neuroimaging or molecular analyses of cerebrospinal fluid or blood plasma.

Accordingly, treatments that promote glymphatic flow may be beneficial for treating these neurodegenerative diseases. However, existing approaches to promoting glymphatic flow are based upon a limited or incomplete understanding of the effects of pharmaceuticals on glymphatic flow and have been carried out in rodents without the translational clinical studies needed to confirm similar mechanism-of-action and efficacy in humans.

As one example, U.S. Pat. No. 9,901,650 to Nedergaard et al. describes administration of pharmaceutical agents for increasing glymphatic clearance. As one example, Nedergaard describes the administration of sleep aids to treat insomnia and thereby increase glymphatic clearance. Nedergaard provides a lengthy list of a variety of sleep aids, including antihistamines, benzodiazepines, non-benzodiazepines, and barbiturates, but provides little explanation of the mechanisms by which these various sleep aids affect the glymphatic system nor does she provide any clinical trial data supporting her claims.

In another example, PCT Publication No. WO2024/023261 to Fritsche describes the treatment of sleep disorders with the administration of dexmedetomidine. Fritsche further explains that the treatment of sleep disorders with dexmedetomidine also can be beneficial for other disorders associated with poor sleep, including heart, lung, and neurodegenerative disorders. However, Fritsche makes no mention of the glymphatic system or the mechanisms by which dexmedetomidine affects the glymphatic system.

Another recent paper titled "Could dexmedetomidine be repurposed as a glymphatic enhancer?", Persson, et al., Trends in Pharmacological Sciences, December 2022, Vo. 43, No. 12, describes a study involving dexmedetomidine and glymphatic flow in rodents. The study described in the Persson paper found that administering dexmedetomidine promoted glymphatic influx of CSF tracers into the brain parenchyma in rodents. However, the Persson paper acknowledges that "the effects of dexmedetomidine on cerebral arteries are not completely understood" (Persson, p. 1034). The rodent study in Persson as well as other studies have focused on the effect of dexmedetomidine when a loading dose is administered that is 15 times higher than the maximum recommended FDA loading dose and when the steady-state infusion dose per kilogram is 15 to 20 times higher than the maximum recommended FDA maintenance dose in humans (Persson, p. 1034 and footnote 32; USFDA prescribing label for dexmedetomidine hydrochloride; Reference ID: 3836249 at https://www.fda.gov/drugsatfda).

As will be described further below, Applicant has unexpectedly discovered that prior understandings of the effect of dexmedetomidine on glymphatic flow are incomplete. By focusing on a loading dose of dexmedetomidine and infusion doses that are both substantially greater than the maximum human recommended FDA loading and maintenance doses, prior studies have failed to appreciate the negative vascular effects of dexmedetomidine at the lower FDA maintenance dose that causes it to fail in promoting glymphatic flow in humans. Applicant has further discovered improved approaches to promoting glymphatic flow by simultaneously targeting a novel mechanistic coupling discovered between the systemic vascular system and glymphatic flow. This coupling is mediated by cerebral vascular autoregulation and its influence on cerebrovascular compliance.

SUMMARY

The present disclosure relates generally to treating neurodegenerative diseases. One example embodiment is directed to a pharmaceutical composition. The pharmaceutical composition can comprise: (a) dexmedetomidine, or a pharmaceutically acceptable salt thereof, and (b) midodrine, or a pharmaceutically acceptable salt thereof.

Another example embodiment pertains to a method of treating one or more symptoms of a neurodegenerative disease. The method can comprise: (a) administering to a subject in need thereof an effective amount of dexmedetomidine, or a pharmaceutically acceptable salt thereof, and (b) administering to the subject an effective amount of midodrine, or a pharmaceutically acceptable salt thereof.

Yet another example embodiment is directed to a pharmaceutical formulation. The pharmaceutical formulation can comprise: (a) dexmedetomidine, or a pharmaceutically acceptable salt thereof, (b) midodrine, or a pharmaceutically acceptable salt thereof, and (c) at least one pharmaceutically acceptable carrier or pharmaceutically acceptable excipient.

Yet another example embodiment pertains to a pharmaceutical composition. The pharmaceutical composition can comprise: (a) midodrine, or a pharmaceutically acceptable salt thereof, and (b) a prodrug compound that achieves a blood concentration of one of dexmedetomidine, or a pharmaceutically acceptable salt thereof, in a subject in the range of 100 pg/mL to 2000 pg/mL.

The foregoing embodiments are non-limiting examples and other aspects and embodiments will be described herein. The foregoing summary is provided to introduce various concepts in a simplified form that are further described below in the detailed description. This summary is not intended to identify required or essential features of the claimed subject matter nor is the summary intended to limit the scope of the claimed subject matter.

BRIEF DESCRIPTION OF THE DRAWINGS

The specific features, aspects and advantages of the present disclosure will become better understood with regard to the following description and accompanying drawings.

FIG. 2 provides an enlarged illustration of brain perivascular and interstitial spaces in which glymphatic flow is clearing waste.

FIG. 3 provides a table of data for Study 1 in which dexmedetomidine was administered to human subjects.

FIG. 4 provides a table of data for Study 2 in which a combination of dexmedetomidine and midodrine was administered to human subjects.

DETAILED DESCRIPTION OF EXAMPLE EMBODIMENTS

Overview of Glymphatic Function

Figure 1:
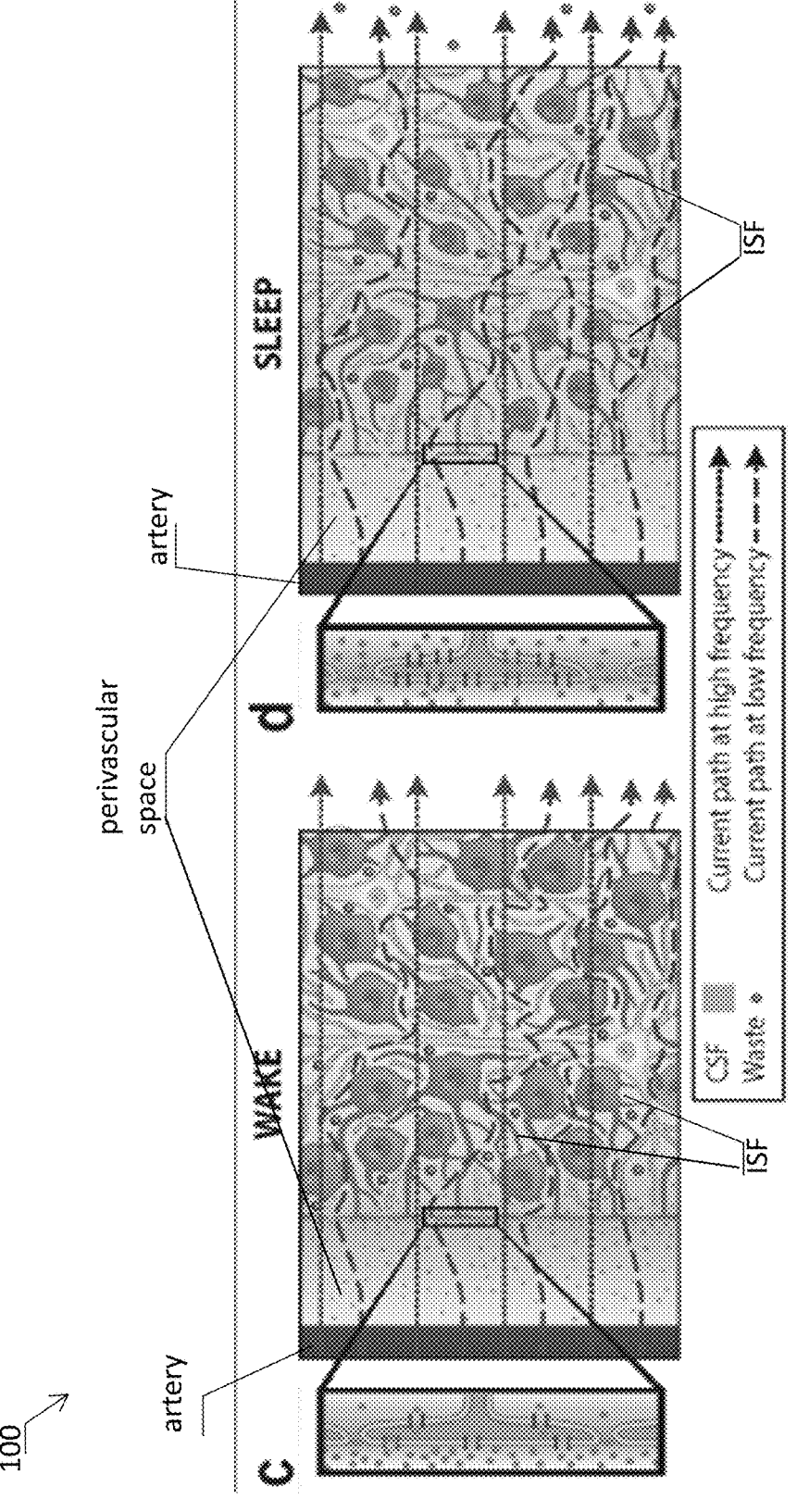
FIG. 1 provides illustrations of brain perivascular and interstitial spaces in a subject during wake and sleep states.

Referencing the glymphatic flow responsible for the clearance of proteins described above and as illustrated in FIGS. 1 and 2, the perivascular spaces (PVS) of the brain are central to the glymphatic fluid transport system. Fluorescent dye-labeled particles that enable visualization of the perivascular spaces in rodents reveal that the system comprises periarterial, pericapillary, and perivenular spaces all interconnected into a single network. The glymphatic flow system clears brain interstitial fluid (ISF) waste products such as the proteinopathy proteins through the perivenular spaces of veins to exit the central nervous system (CNS) into meningeal lymphatics and along exiting perineural and perarteriolar sheaths. The PVS is a site of great importance that is affected by disease processes such as cerebral amyloid angiopathy characterized by perivascular amyloid beta deposits and present in over 90% of Alzheimer's disease brains. PVS accumulation of p-tau is also observed in Alzheimer's disease and has been demonstrated to be present in arteries, arterioles and veins in the brain. In the glymphatic flow system, cerebrospinal fluid (CSF) enters the periarterial spaces, running in the direction of the blood flow and propelled by arterial wall pulsations. As noted in FIG. 2, CSF enters the brain parenchyma and mixes with ISF facilitated by aquaporin-4 (AQP4) water channels that are present at the vascular astrocytic endfeet forming the outer wall of the perivascular spaces and by gaps between the endfoot processes. Arterial wall pulsations are the motive force that drive CSF bulk flow through the PVS towards the brain. During sleep, the interstitial spaces in the brain widen by as much as 60% as astrocytes transfer fluid from intracellular to the extracellular space, expanding those spaces and reducing the resistance to flow. This process has been shown to be highly dependent on different elements of sleep physiology and cardiovascular physiology. With modern neuroimaging techniques, it is now possible to visualize CSF flow out of the fourth ventricle in the intact CNS by the second-to-second pulsatile movement of CSF through the cerebral aqueduct occurring with each cardiac contraction. Respirations further contribute to this rhythm, adding pulsations at a lower frequency. Superimposed on these acute pulsations is a circadian or diurnal rhythm with maximum CSF production occurring at night during sleep and minimum occurring in the afternoon. MRI studies in animal models using CSF tracers reveal that the glymphatic flow from ISF to subarachnoid CSF is enhanced during NREM sleep.

The concentration of amyloid-$\beta$ and tau in the interstitial space and CSF follow a diurnal pattern with both protein concentrations reaching their peak during wakefulness and trough following sleep. A single night of sleep deprivation results in a significant increase in soluble amyloid-$\beta$ in the brain ISF demonstrated with positron emission tomography (PET) using an amyloid-binding radiotracer. The net concentration of amyloid-$\beta$, tau and other proteins in the CSF and ISF reflect the combined effects of diurnal- and state-dependent variations in CSF production rate, ISF volume, ISF turnover rate, and glymphatic clearance. Glymphatic clearance depends on the integrity of three key physiologies: astrocyte modulation of brain parenchymal resistance, neurovascular compliance and sleep neurophysiology.

Poor sleep and sleep deprivation result in reduced glymphatic clearance by disrupting all three key physiologies and leads to the accumulation of waste solutes including amyloid-$\beta$ solutes and other proteins in the brain.

During sleep, glymphatic flow is increased by the action of astrocytes that are responsible for widening the interstitial spaces by shifting intracellular fluid to the extracellular space. Using membrane channel protein AQP4 and water flux through AQP4, astrocytes can shrink their cell volume to increase ISF space. Pre-clinical rodent findings have shown an increase in ISF space of 60% during sleep enabling water and solutes to diffuse into adjacent perivascular spaces. FIG. 1 provides comparative illustrations of the ISF space while a subject is asleep and while the subject is awake. As can be seen in the illustration on the right, the ISF space has increased substantially during sleep. During slow-wave sleep, the increase in ISF space, the opening of gap junction of astrocyte end-feet and an increase in cerebral hemodynamics creates an environment for exchange of nutrients and elimination of waste between ISF and CSF.

Studies with rodents have shown short term disruption in sleep causes an increase in CSF and ISF waste proteins and long-term disruption leads to formation of ISF protein aggregates with neurodegeneration. Additionally, damage to molecular and cellular components of the glymphatic flow system, to the brain neurovascular integrity and to its neurovascular coupling that occurs with aging, chronic co-morbidities, neurodegenerative diseases and physical brain trauma are closely linked to an increase of tau and amyloid-$\beta$ in extracellular fluids. The spread of these aggregated proteins in the brain parenchyma leads to worsening neurodegeneration and clinical symptoms including decline in cognition.

The glymphatic system of waste clearance operates during sleep and is partially dependent on features measurable with sleep electroencephalogram (EEG) and on features that measure neurovascular compliance, pulsation and coupling. As described further below, it is possible to assess glymphatic function by measuring the resistance to glymphatic flow in the interstitial spaces in the brain that are regulated by astrocytes.

In connection with the studies described below, cardiac stroke volume and heart rate also affect the glymphatic system. With each heartbeat, a large fraction of the cardiac output is ejected into the internal carotid and vertebral arteries and delivered to the brain. Higher levels of norepinephrine during wake or sleep, activated by the locus coeruleus in the brain, decreases brain interstitial fluid flow and protein biomarker clearance. Higher sleep heart rate also leads to less glymphatic flow and protein clearance. Lower sleep resting heart rate is compensated by higher cardiac stroke volume to maintain the cardiac output and tightly regulated cerebral blood flow. A higher cardiac stroke volume results in larger cerebral perfusion pulsations and increases the propelling forces of glymphatic flow. Higher cerebral vascular compliance, independent of cardiac stroke volume, translates a given stroke volume of blood into a greater arterial wall pulsation, delivering a greater propelling force of the CSF in the adjacent PVS. Conversely, diseases that harden arteries, in particular the arterioles that penetrate the brain parenchyma alongside which run the perivascular spaces containing cerebrospinal fluid that is propelled into the brain parenchyma to drive glymphatic flow, decrease the propelling forces. A decrease in the propelling force is measured by a decrease in the magnitude of the cerebral perfusion pulsation. Changes in respiratory rate also alter the blood volume pulsations by affecting venous return to the heart and thereby changing cardiac stroke volume. Importantly, as demonstrated by our reported human clinical trials, cerebral vascular autoregulation, which dilates or constricts neurovascular arteries in response to systemic blood pressure, transiently affects cerebral vascular compliance and, in turn, influences the motive force propelling cerebrospinal fluid (CSF) along the perivascular space (PVS), independently of cardiac stroke volume.

Unexpected Phenomena

As referenced above in connection with the Persson paper, there is a conventional belief that administration of dexmedetomidine improves glymphatic flow, but the mechanism has not been completely understood. Dexmedetomidine is an alpha-2A adrenergic agonist which interacts with alpha-2A adrenergic receptors located in the locus coeruleus in the brainstem to shut off norepinephrine production. While not yet tested in humans, the conventional belief is that administration of dexmedetomidine causes a shift in fluid from intracellular (astrocytes) to extracellular, thereby causing enlargement of the brain parenchymal interstitial space. However, this understanding of the effect of dexmedetomidine is incomplete because the conventional approach has focused on the effects when a loading dose of dexmedetomidine is administered in rodent studies that is 10 times higher than the human recommended loading dose followed by a maintenance infusion that was 10 to 20 times higher than recommended human maintenance infusion. At the FDA recommended plasma concentrations, dexmedetomidine causes hypotension but at high plasma concentrations associated with an exceedingly high loading dose or high maintenance infusions, dexmedetomidine has off-target effects which bind to alpha-1 adrenergic receptors and alpha-2B receptors, both causing vasoconstriction and hypertension. This compensatory vasoconstriction masks the negative vasodilation effect of dexmedetomidine's alpha-2A target that at lower doses leads to hypotension and impairs glymphatic flow.

The drop in norepinephrine production caused by dexmedetomidine's alpha-2A agonist effect induces hypotension and bradycardia systemically which results in a cerebral blood flow autoregulatory response. This autoregulatory response causes neurovascular vasodilation, decreases neurovascular compliance and compresses the perivascular spaces (PVS) along the penetrating arteries and veins of the brain. The net results are smaller amplitude arterial pulsations and higher PVS resistance pathways of CSF from the ventricles down to the astrocytic end-feet walls surrounding the brain parenchyma from which CSF would enter into the expanded interstitial spaces. The systemic hypotension also reduces the cardiac stroke volume which in turn reduces the stroke volume of the brain CSF ventricles which reduces the pulse pressure gradient to push CSF along the PVS. Our investigation discovered these unexpected negative effects of dexmedetomidine on glymphatic flow as evidenced by the data of Study 1 described below.

Our investigation further discovered that we are able to reverse the negative effects of dexmedetomidine on glymphatic flow by administering an alpha-1 adrenergic agonist that acts peripherally without crossing the blood-brain barrier, such as midodrine at an FDA recommended dose, in combination with the dexmedetomidine. The dexmedetomidine crosses the blood-brain barrier of the subject while the midodrine does not cross the blood-brain barrier. The dexmedetomidine and the midodrine work synergistically whereby the midodrine counteracts the negative cardiovascular effects, e.g., hypotension and bradycardia, of the dexmedetomidine. By reversing the systemic vascular effects of dexmedetomidine we eliminate the cerebral vascular autoregulatory response, preserve the neurovascular compliance, preserve the CSF ventricular pressure gradient from each cardiac stroke volume and further preserve the low resistance in the perivascular spaces in the brain. This further discovery is illustrated by the data of Study 2 described below.

We further propose that improved glymphatic flow can be achieved by administering to a subject a combination of an alpha-2A adrenergic agonist and an alpha-1 adrenergic agonist where the alpha-2A adrenergic agonist crosses the blood-brain barrier of the subject while the alpha-1 adrenergic agonist does not cross the blood-brain barrier. The combination of the alpha-2A adrenergic agonist and an alpha-1 adrenergic agonist has a synergistic effect whereby the alpha-1 adrenergic agonist acts systemically to counteract the systemic vascular effects, e.g., hypotension and bradycardia, of the alpha-2A adrenergic agonist. Both the alpha-2A adrenergic agonist and the alpha-1 adrenergic agonist must have similar pharmacokinetics, including time to maximum plasma concentration, so that a fixed-dose combination of both drugs can be administered to control the systemic vascular effects of the alpha-2A agonist.

Comparative Data of Glymphatic Flow

The following description concerns two studies that illustrate the surprising discoveries with respect to the effects of dexmedetomidine on glymphatic flow. Study 1 concerns the administration of dexmedetomidine to a group of human subjects. Study 2 concerns the administration of a combination of dexmedetomidine and midodrine to a group of human subjects. Both Study 1 and Study 2 involve using a head-mounted device to measure parenchymal resistance to glymphatic flow. The use of this head-mounted device is described further in Dagum, Paul, et al.; A wireless device for continuous measurement of brain parenchymal resistance tracks glymphatic function in humans; Nature Biomedical Engineering; May 27, 2025; https://doi.org/10.1038/s41551-025-01394-9.

Figure 3:
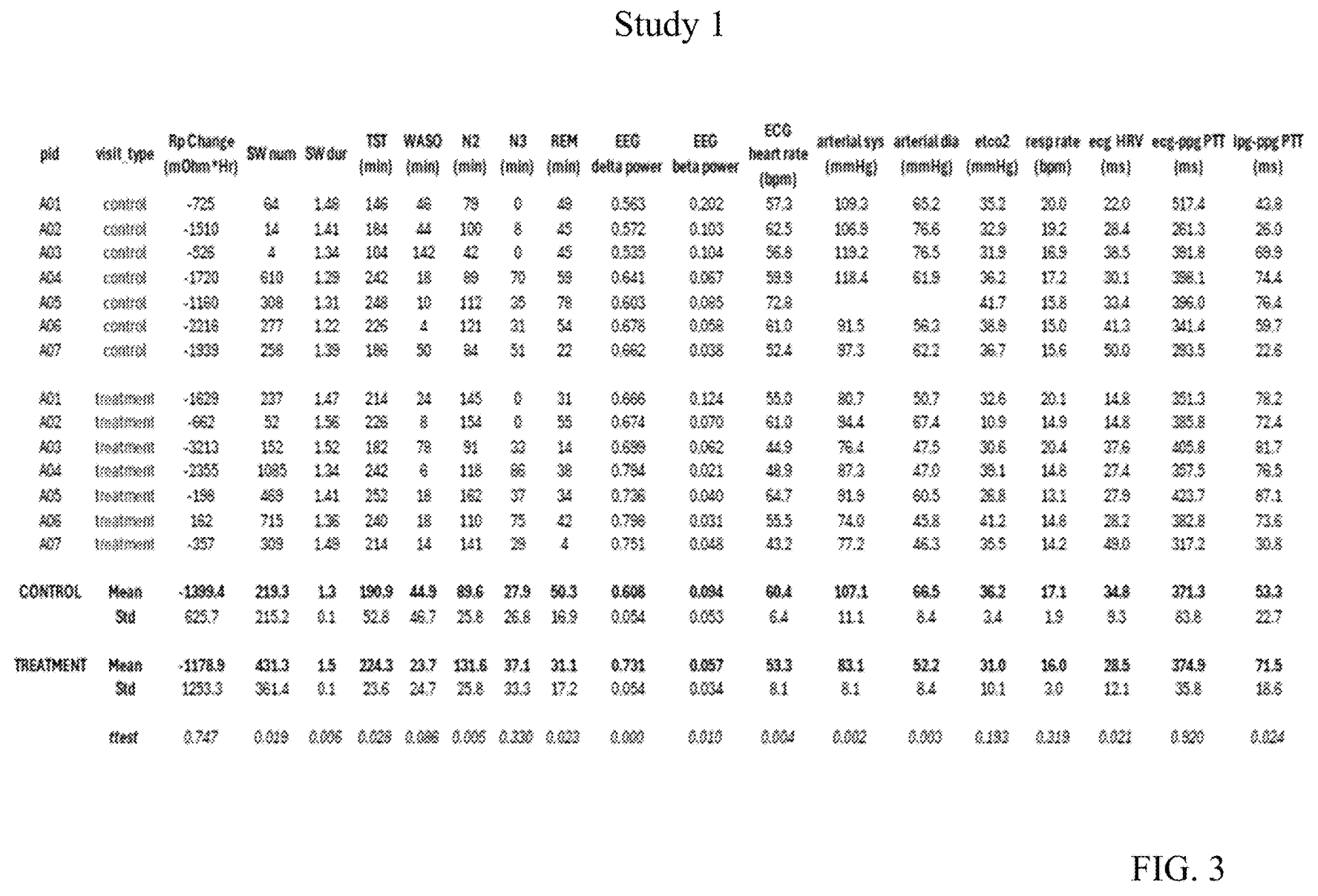

The data for Study 1 shows that, as indicated in the column labeled Rp Change in the data attached at FIG. 3, subjects receiving dexmedetomidine during the treatment visit exhibited greater parenchymal resistance (Rp) to glymphatic flow than when the subjects received saline during the control visit. Thus, the data for Study 1 indicates the administration of dexmedetomidine alone is counterproductive to the goal of increasing glymphatic flow. This result from the Study 1 data is surprising and contrary to the generally held belief, as described in the Persson paper referenced above, that administration of dexmedetomidine improves glymphatic flow.

Notable results from the data of Study 1 include the slow wave number and their period length, both of which increased with dexmedetomidine, indicating that dexmedetomidine would appear to improve sleep as measured by EEG physiology. The effect of dexmedetomidine on the EEG hypnogram includes increase in N2 sleep duration and a decrease in REM sleep duration. The effect of dexmedetomidine on EEG band powers include an increase in EEG delta power (0.5-4 Hz), and a decrease in EEG beta power, consistent with improved sleep physiology measured by EEG. But dexmedetomidine worsened neurovascular physiology that as demonstrated by our clinical studies is critical to increase glymphatic flow. With respect to vascular effects, the data shows dexmedetomidine causing a decrease in heart rate, systolic blood pressure, and diastolic blood pressure. These vascular changes trigger a baroreceptor sympathetic outflow to attempt to restore systemic pressure. This is evidenced by the decrease in heart-rate variability (HRV) that is associated with higher peripheral sympathetic tone, and that peripheral pulse-transit time (PTT) measured from the QRS peak of the ECG and the peak of device PPG measured in the ear remains unchanged. Under normal cardiovascular physiology, lower blood pressure associates with an increase in PTT but in this case, the baroreceptor compensatory response lead to peripheral arterial stiffening and blunting of an increase in PTT. In contrast to the systemic effects, the drop in vascular perfusion pressure of the brain triggered an autoregulatory response causing vasodilation in the brain as described above. This is evidenced by the increase in the ipg-ppg PTT time. This metric measures the time difference between the peak of the impedance-plethysmogram (IPG) captured by the device and the peak of the in-ear PPG. The IPG measures intracranial vascular pulsations and its peak occurs earlier than the in-ear PPG peak. Hence an increase in the ipg-ppg PTT time signifies that the IPG peak moves even earlier as would be consistent with decreased neurovascular compliance. The alternative explanation that the in-ear PPG occurs later is eliminated as noted above because the ecg-ppg PTT time does not change. In both Study 1 and Study 2, a loading dose of dexmedetomidine was not used and the maintenance dose was within the recommended FDA dose. Thus, no off-target effects counteracting the negative neurovascular effects of dexmedetomidine occurred in Study 1 and 2.

Figure 4:
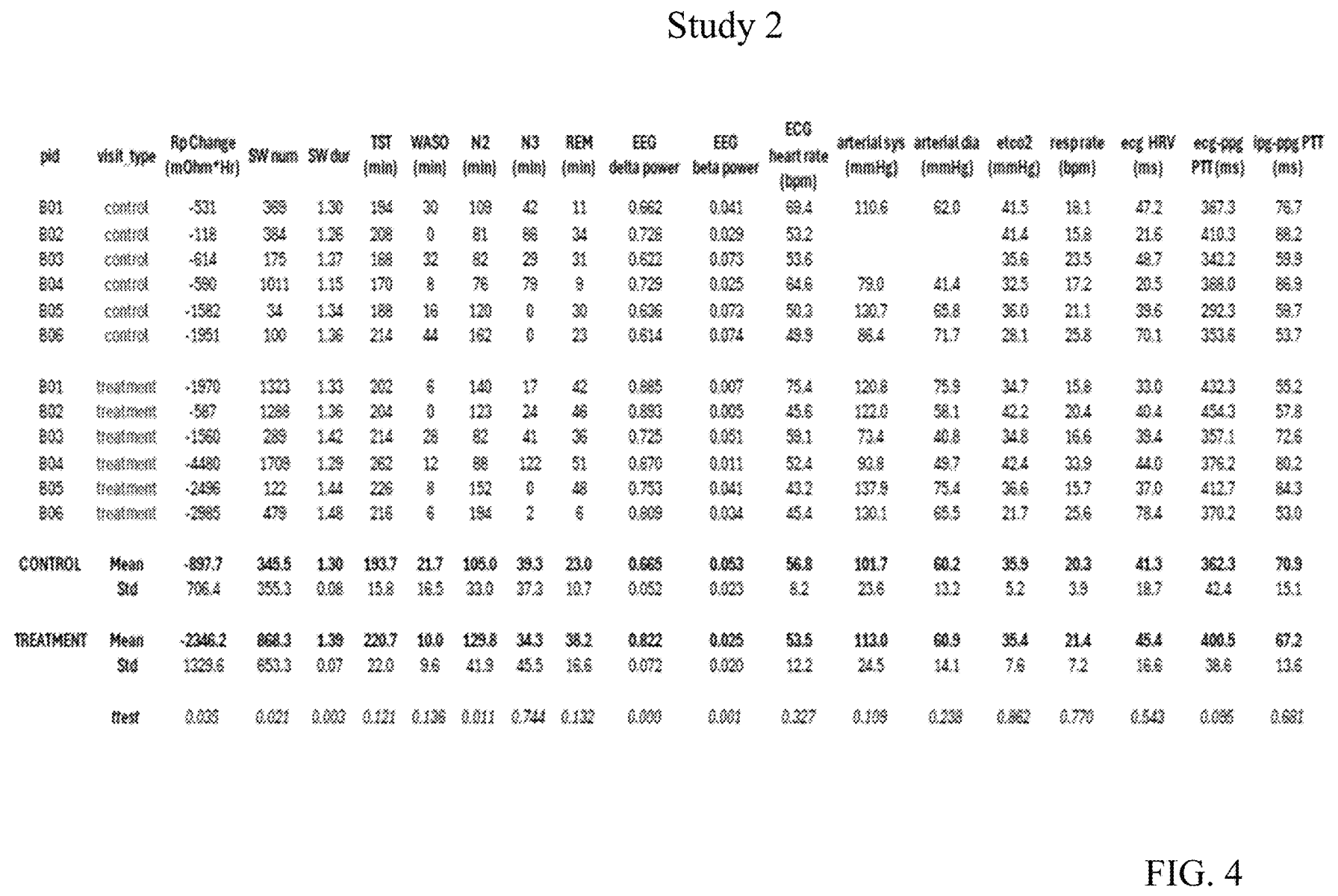

The data for Study 2 shows a synergistic effect produced by the administration of dexmedetomidine and midodrine to subjects. The data for Study 2 demonstrated that, as indicated in the column labeled Rp Change in the data attached at FIG. 4, the administration of dexmedetomidine and midodrine in combination reduces resistance to glymphatic flow by more than two times relative to the control visit data when only saline and a placebo were administered. The effects of the dexmedetomidine and the effects of the midodrine work in concert to reduce resistance to glymphatic flow in the subjects thereby increasing glymphatic clearance.

Other data collected in Study 2 also reflect improvements in parameters associated with improved glymphatic flow relative to the data collected in Study 1. Similar to Study 1, the treatment data in Study 2 showed increases in the slow wave number and duration, increase in the duration of N2 sleep, greater EEG delta power (0.5-4 Hz) and significant decreases in the EEG beta power, all indicating improved sleep based on EEG physiology. In contrast to Study 1, Study 2 showed the peripheral vascular improvements attributable to midodrine in that heart rate, systolic blood pressure, diastolic blood pressure, end-tidal carbon dioxide, and respirations rate did not change significantly. Importantly, we note that in Study 2, there is no change in HRV because there is no increase in peripheral sympathetic outflow in response to dexmedetomidine when administered with midodrine, and further there is no change in either the peripheral ecg-ppg PTT time or the ipg-ppg PTT time that measures neurovascular compliance. Thus, in Study 2, midodrine prevented peripheral vascular hypotension that in Study 1 lead to a systemic baroreceptor increase in sympathetic outflow noted in Study 1's decrease in HRV but that was inadequate to compensate the hypotension and resulted in cerebral vascular autoregulation that led to a decrease in neurovascular compliance measured by the ipg-ppg PTT.

Study Protocol

Study 1 and Study 2 were conducted under the same testing protocol, with the exception that midodrine was administered in Study 2. The studies were conducted as randomized cross-over repeated measures studies. The subjects in the studies participated in two visits, a control visit and a treatment visit, with the visits scheduled 2 to 4 weeks apart. Prior to each visit, participants were required to remain awake overnight and monitored by a nurse. At each visit the participants are attached to an intravenous catheter, an arterial pressure line, electrocardiograph, end-tidal-CO2 via nasal canula, and a glymphatic flow monitoring device that measures brain parenchymal resistance, EEG and neurovascular compliance, continuously. Examples of glymphatic flow monitoring devices are described in U.S. Pat. Nos. 11,478,184 and 12,004,874. During each visit, the participants lay supine for 5 hours, with the first 15 minutes maintained in an awake state to establish a baseline, followed by a 4-hour and 15-minute sleep opportunity. In Study 1, during the control visit, saline was administered via the intravenous catheter, whereas during the treatment visit, dexmedetomidine was administered via the intravenous catheter. In Study 2, a placebo tablet was administered 45 minutes before beginning the saline intravenous infusion during the control visit, whereas, during the treatment visit, a 10 mg tablet of midodrine was administered 45 minutes before beginning the dexmedetomidine intravenous infusion. At the conclusion of the 4-hour and 15-minute sleep opportunity in each study, the participants were awakened and instructed to remain supine for the final 30 minutes of the study period.

Additional Supporting Data

Figure 5:
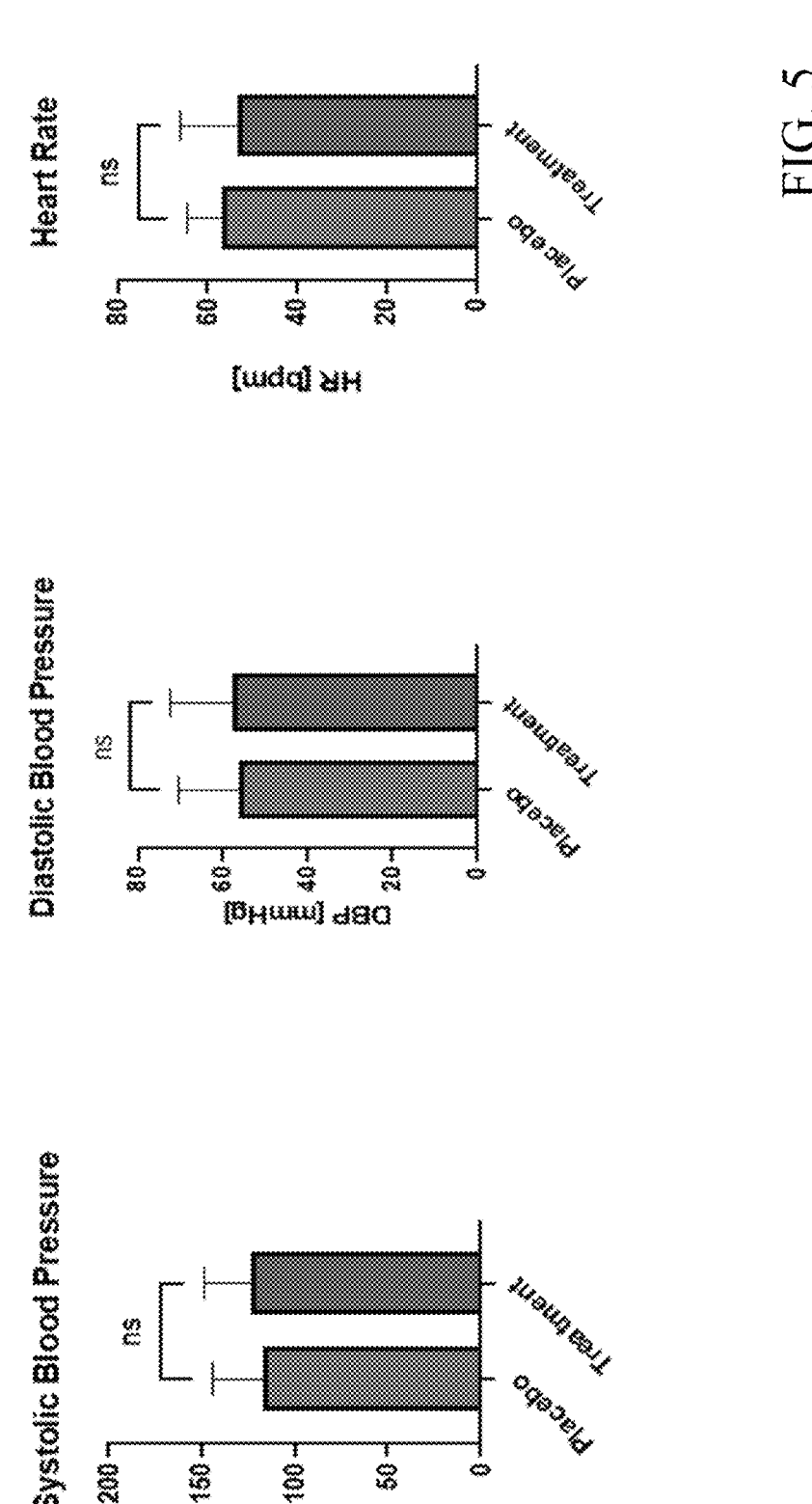
FIG. 5 provides data illustrating an alpha-1 adrenergic agonist, midodrine, mitigating the negative systemic vascular effects caused by administration of an alpha-2A adrenergic agonist, dexmedetomidine, in human subjects.
Figure 6:
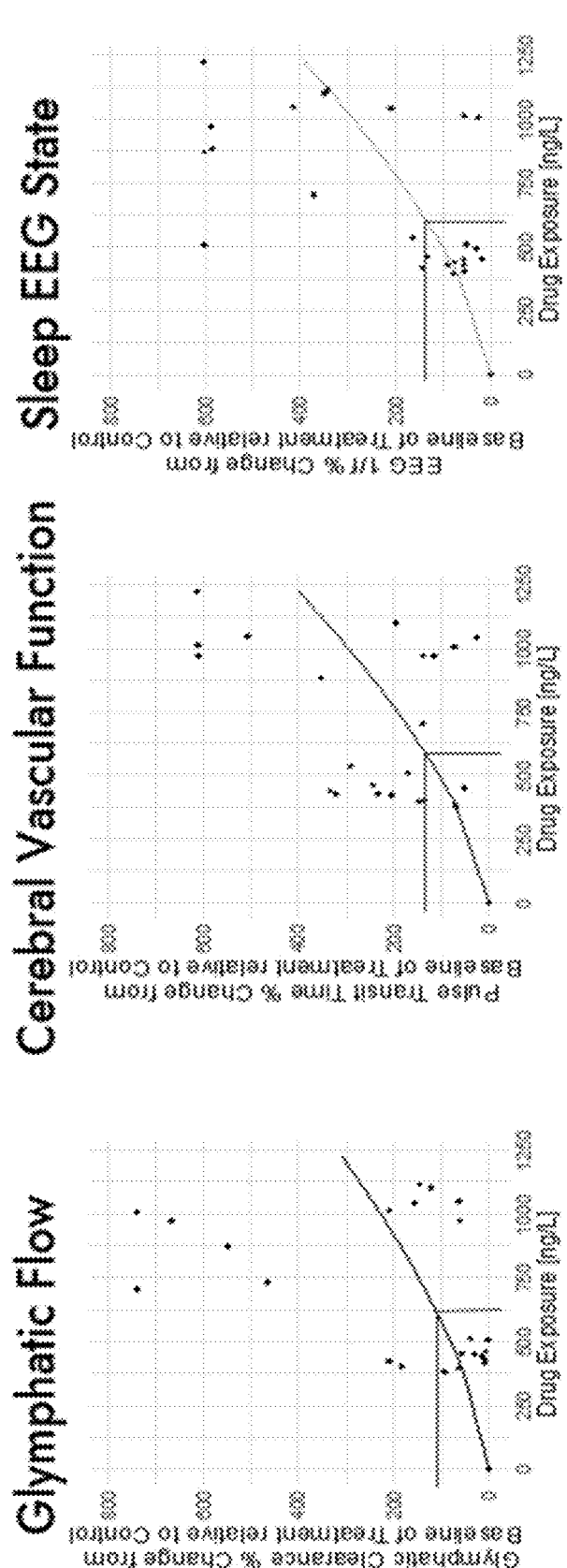
FIG. 6 provides data gathered from another study in which a combination of dexmedetomidine and midodrine was administered to human subjects.

FIGS. 5 and 6 provide additional data supporting the foregoing conclusions regarding the administration of an alpha-1 adrenergic agonist, such as midodrine, and an alpha-2A adrenergic agonist, such as dexmedetomidine. This data pools the Study 2 data with new participants undergoing the same study protocol at the same dexmedetomidine and midodrine doses for a total of 18 participants. FIG. 5 illustrates the cardiovascular benefit of administering midodrine in combination with dexmedetomidine. Specifically, FIG. 5 demonstrates that midodrine mitigates the negative cardiovascular effects that would be caused by administering dexmedetomidine alone. The data illustrated in FIG. 6 demonstrates that the combined administration of dexmedetomidine and midodrine enhances three features driving glymphatic clearance-reduces glymphatic parenchymal resistance to flow, increases cerebral vascular compliance, and improves sleep EEG physiology. An analysis of the plasma of participants in this study also demonstrated an increase in the clearance of amyloid beta and tau proteins from the brain to the blood with the increase in glymphatic clearance. The analysis demonstrated an increase in the Abeta-42/Abeta-40 ratio of 11.7% after dexmedetomidine and midodrine enhanced sleep compared to placebo enhanced sleep and an increase in the phosphorylated-to-non-phosphorylated tau-217 (p-Tau217/n-Tau217) of 16.7%. Notably, administration of dexmedetomidine without midodrine in Study 1 did not increase the clearance of amyloid beta and tau proteins from the brain to the blood as would be expected since glymphatic clearance did not improve over placebo enhanced sleep.

Figure 7:
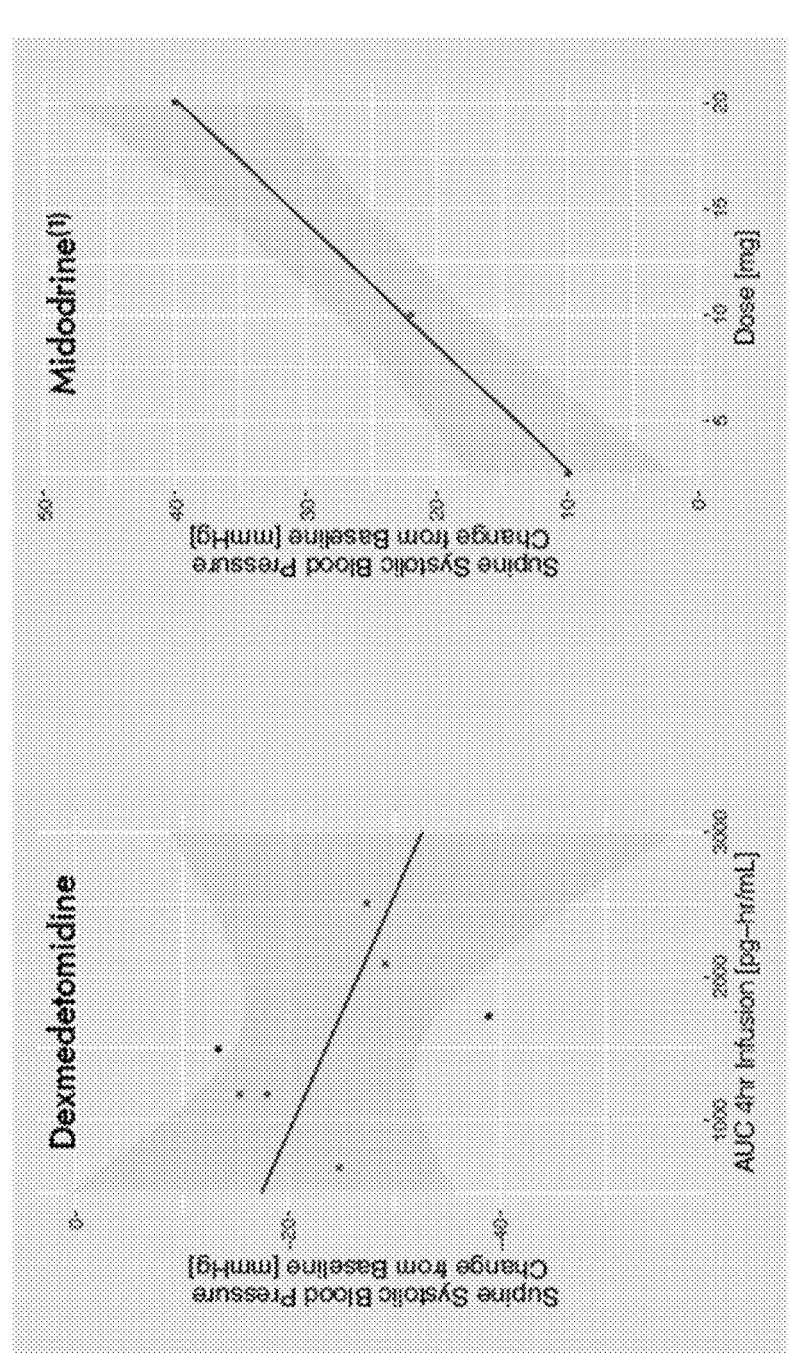
FIG. 7 illustrates human blood pressure curves responsive to the administration of dexmedetomidine and midodrine.

FIG. 7 illustrates blood pressure curves responsive to the administration of dexmedetomidine and midodrine. The required dose of midodrine at a particular dose level of dexmedetomidine can be determined by analyzing the blood pressure response curves because of the similar pharmacokinetics of both drugs. The source of the blood pressure response curve for midodrine is: Wright, R. A., et al. "A double-blind, dose-response study of midodrine in neurogenic orthostatic hypotension." Neurology 51.1 (1998): 120-124.

Example Embodiments of Pharmaceutical Promotion of Glymphatic Function

The following example embodiments are set forth without any loss of generality to, and without imposing limitations upon, the claimed inventions.
Pharmaceutical Compositions of Dexmedetomidine and Midodrine The present disclosure provides pharmaceutical compositions comprising dexmedetomidine, or a pharmaceutically acceptable salt thereof, and midodrine, or a pharmaceutically acceptable salt thereof. In an example embodiment, the pharmaceutical composition comprises an amount of dexmedetomidine, or a pharmaceutically acceptable salt thereof, and an amount of midodrine, or a pharmaceutically acceptable salt thereof, that are effective for improving glymphatic flow in the brain of a subject. In another example embodiment, the pharmaceutical composition comprises an amount of dexmedetomidine, or a pharmaceutically acceptable salt thereof, and an amount of midodrine, or a pharmaceutically acceptable salt thereof, that are effective for treating neurodegenerative disease in a subject, including dementia, Alzheimer's disease, and Parkinson's disease.

In one aspect, the pharmaceutical composition may comprise an amount of dexmedetomidine or pharmaceutically acceptable salt thereof that is in the range of 40 micrograms to 400 micrograms and an amount of midodrine or pharmaceutically acceptable salt thereof that is in the range of 2 milligrams to 15 milligrams. In a further embodiment, the pharmaceutical composition may comprise an amount of dexmedetomidine or pharmaceutically acceptable salt thereof that is in the range of 80 micrograms to 300 micrograms and an amount of midodrine or pharmaceutically acceptable salt thereof that is in the range of 5 milligrams to 13 milligrams. In yet another embodiment, the pharmaceutical composition may comprise an amount of dexmedetomidine or pharmaceutically acceptable salt thereof that is in the range of 100 micrograms to 200 micrograms and the amount of midodrine or pharmaceutically acceptable salt thereof is in the range of 7 milligrams to 12 milligrams. In certain embodiments of the foregoing compositions and mode of delivery, the dexmedetomidine or pharmaceutically acceptable salt thereof may exhibit a bioavailability of 10% to 100%, or 30% to 95%, or 50% to 90%. Similarly, in certain embodiments of the foregoing compositions, the midodrine or pharmaceutically acceptable salt thereof may exhibit a bioavailability of 50% to 99%, or 50% to 95%, or 50% to 90%.

In another aspect, the pharmaceutical composition may comprise an amount of dexmedetomidine or pharmaceutically acceptable salt thereof that achieves a blood concentration in a subject in the range of 100 pg/mL to 2000 pg/mL and an amount of midodrine (which is a prodrug) or pharmaceutically acceptable salt thereof that achieves a blood concentration of the active metabolite desglymidodrine in the subject in the range of 5 ng/mL to 100 ng/ml. In a further embodiment, the pharmaceutical composition may comprise an amount of dexmedetomidine or pharmaceutically acceptable salt thereof that achieves a blood concentration in a subject in the range of 150 pg/mL to 1500 pg/mL and an amount of midodrine or pharmaceutically acceptable salt thereof that achieves a blood concentration of the active metabolite desglymidodrine in the subject in the range of 10 ng/mL to 75 ng/mL. In yet another embodiment, the pharmaceutical composition may comprise an amount of dexmedetomidine or pharmaceutically acceptable salt thereof that achieves a blood concentration in a subject in the range of 200 pg/mL to 1000 pg/mL and an amount of midodrine or pharmaceutically acceptable salt thereof that achieves a blood concentration of the active metabolite desglymidodrine in the subject in the range of 20 ng/ml to 50 ng/mL.

In another aspect wherein the pharmaceutical composition is administered through the gastrointestinal tract, the amounts of dexmedetomidine in the composition are increased. In such an embodiment, the pharmaceutical composition may comprise an amount of dexmedetomidine or pharmaceutically acceptable salt thereof that is in the range of 240 micrograms to 2,400 micrograms and an amount of midodrine or pharmaceutically acceptable salt thereof that is in the range of 2 milligrams to 15 milligrams. In a further embodiment, the pharmaceutical composition may comprise an amount of dexmedetomidine or pharmaceutically acceptable salt thereof that is in the range of 480 micrograms to 1,800 micrograms and an amount of midodrine or pharmaceutically acceptable salt thereof that is in the range of 5 milligrams to 13 milligrams. In yet another embodiment, the pharmaceutical composition may comprise an amount of dexmedetomidine or pharmaceutically acceptable salt thereof that is in the range of 600 micrograms to 1,200 micrograms and the amount of midodrine or pharmaceutically acceptable salt thereof is in the range of 7 milligrams to 12 milligrams.

In any of the foregoing example pharmaceutical compositions comprising dexmedetomidine and midodrine, the pharmaceutical composition may further comprise one or more pharmaceutically acceptable carriers. As examples, the pharmaceutically acceptable carriers may be selected from the group consisting of a liposome, a polymer matrix, a sugar, a starch, cellulose, a wax, a polyol, a buffering agent, agar, and a saline solution.

In any of the foregoing example pharmaceutical compositions, the dexmedetomidine, or pharmaceutically acceptable salt thereof, and the midodrine, or pharmaceutically acceptable salt thereof, are provided as separate components of the pharmaceutical composition.

In any of the foregoing example pharmaceutical compositions, the dexmedetomidine, or pharmaceutically acceptable salt thereof, and the midodrine, or pharmaceutically acceptable salt thereof, are provided as integrated components of the pharmaceutical composition.

In any of the foregoing example pharmaceutical compositions, the pharmaceutical composition may be provided in a dosage form selected from the group consisting of a film, a wafer, a patch, a lozenge, a gel, a spray, a tablet, a capsule, a suppository, a powder, and a liquid drop.

In any of the foregoing example pharmaceutical compositions, the pharmaceutical composition may be formulated for oral, parenteral, or transmucosal administration.

In an alternative embodiment of any of the foregoing example pharmaceutical compositions, the pharmaceutical composition comprises midodrine, or a pharmaceutically acceptable salt thereof; and, in place of dexmedetomidine, the composition comprises a prodrug compound that achieves a blood concentration of dexmedetomidine, or a pharmaceutically acceptable salt thereof, in a subject in the range of 100 pg/mL to 2000 pg/mL. Using a prodrug compound can be advantageous in maintaining a sustained blood concentration of dexmedetomidine in the subject. The prodrug compound may be derived from dexmedetomidine or an isomer thereof. The midodrine, or pharmaceutically acceptable salt thereof, may achieve a blood concentration of active metabolite desglymidodrine in the subject in the range of 5 ng/ml to 100 ng/mL. Alternatively, the midodrine, or pharmaceutically acceptable salt thereof, is present in the composition in the range of 2 milligrams to 15 milligrams.

In any of the foregoing example pharmaceutical compositions, the dexmedetomidine, or a pharmaceutically acceptable salt thereof, and the midodrine, or pharmaceutically acceptable salt thereof, are present in an effective amount to treat one or more symptoms of a neurodegenerative disease, including dementia, Alzheimer's disease, and Parkinson's disease.

Formulations Comprising Dexmedetomidine and Midodrine

The present disclosure provides formulations that deliver a therapeutically effective amount of the foregoing disclosed compositions comprising dexmedetomidine, or pharmaceutically acceptable salt thereof, and the midodrine, or pharmaceutically acceptable salt thereof, to a subject. The formulations comprising the disclosed compositions may be formulated for oral, parenteral, or transmucosal administration. More specifically, the formulations comprising the disclosed compositions may have a dosage form selected from the group consisting of a film, a wafer, a patch, a lozenge, a gel, a spray, a tablet, a capsule, a suppository, a powder, and a liquid drop.

In one aspect, formulations comprising the disclosed compositions are administered parenterally to avoid degradation by the gastrointestinal tract. Such parenterally administered formulations may be administered by injection, and include, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection.

In another aspect, formulations comprising the disclosed compositions are administered transmucosally to avoid degradation by the gastrointestinal tract. Such transmucosally administered formulations may be administered through the oral mucosa, the sublingual mucosa, the buccal mucosa, the nasal mucosa, or the anal mucosa.

In yet another aspect, formulations comprising the disclosed compositions are administered through the gastrointestinal tract. Such formulations administered through the gastrointestinal tract may comprise an increased amount of the alpha-2 adrenergic agonist and the alpha-1 adrenergic agonist.

In one embodiment, a pharmaceutical formulation is provided that comprises dexmedetomidine or a pharmaceutically acceptable salt thereof; midodrine or a pharmaceutically acceptable salt thereof; and at least one pharmaceutically acceptable carrier or pharmaceutically acceptable excipient. In the foregoing embodiment, the pharmaceutically acceptable salt may be selected from hydrochloride, hydrobromide, sulphate, phosphate or acid phosphate, acetate, maleate, fumarate, lactate, tartrate, citrate and gluconate salt forms. In the foregoing embodiment, the pharmaceutically acceptable excipient may be selected from the group consisting of a diluent, a binder, a dye, a preservative, an antioxidant, a flavoring, and a lubricant. In the foregoing embodiment, the pharmaceutically acceptable carrier is selected from the group consisting of a liposome, a polymer matrix, a sugar, a starch, cellulose, a wax, a polyol, a buffering agent, agar, and a saline solution.

Methods of Treatment With Dexmedetomidine and Midodrine

The present disclosure further provides methods of treatment with the foregoing compositions. The methods of treatment include administering to a subject an effective amount of dexmedetomidine, or a pharmaceutically acceptable salt thereof, and an effective amount of midodrine, or a pharmaceutically acceptable salt thereof, for treating one or more symptoms of a neurodegenerative disease. The methods include administering dexmedetomidine and midodrine in any of the amounts provided in the previously described compositions. In an example embodiment, the method of treatment comprises administering an amount of dexmedetomidine, or a pharmaceutically acceptable salt thereof, and an amount of midodrine, or a pharmaceutically acceptable salt thereof, that are effective for improving glymphatic flow and clearance of neurotoxic waste in the brain of a subject. In another example embodiment, the method of treatment comprises administering an amount of dexmedetomidine, or a pharmaceutically acceptable salt thereof, and an amount of midodrine, or a pharmaceutically acceptable salt thereof, that are effective for treating neurodegenerative disease in a subject, including dementia, Alzheimer's disease, and Parkinson's disease.

In one aspect, the method comprises administering an amount of dexmedetomidine, or a pharmaceutically acceptable salt thereof, and an amount of midodrine, or a pharmaceutically acceptable salt thereof, to the subject simultaneously.

In another aspect, the method comprises administering to the subject an amount of dexmedetomidine, or a pharmaceutically acceptable salt thereof, before administering to the subject an amount of midodrine, or a pharmaceutically acceptable salt thereof.

In yet another aspect, the method comprises administering to the subject an amount of dexmedetomidine, or a pharmaceutically acceptable salt thereof, after administering to the subject an amount of midodrine, or a pharmaceutically acceptable salt thereof.

In any of the foregoing methods of treatment, the method may further comprise administering the dexmedetomidine, or pharmaceutically acceptable salt thereof, and/or midodrine, or pharmaceutically acceptable salt thereof, with one or more pharmaceutically acceptable carriers. As examples, the pharmaceutically acceptable carriers may be selected from the group consisting of a liposome, a polymer matrix, a sugar, a starch, cellulose, a wax, a polyol, a buffering agent, agar, and a saline solution.

In any of the foregoing example methods, the dexmedetomidine, or pharmaceutically acceptable salt thereof, and the midodrine, or pharmaceutically acceptable salt thereof, are administered as separate components of a pharmaceutical composition.

In any of the foregoing example methods, the dexmedetomidine, or pharmaceutically acceptable salt thereof, and the midodrine, or pharmaceutically acceptable salt thereof, are administered as integrated components of the pharmaceutical composition.

In any of the foregoing example methods, the dexmedetomidine, or pharmaceutically acceptable salt thereof, and the midodrine, or pharmaceutically acceptable salt thereof, may be provided in a dosage form selected from the group consisting of a film, a wafer, a patch, a lozenge, a gel, a spray, a tablet, a capsule, a suppository, a powder, and a liquid drop.

In any of the foregoing example methods, the dexmedetomidine, or pharmaceutically acceptable salt thereof, and the midodrine, or pharmaceutically acceptable salt thereof, may be formulated for oral, parenteral, or transmucosal administration.

In an alternative embodiment of any of the foregoing example methods, in place of administering dexmedetomidine, the effective amount of dexmedetomidine is achieved by administration of a prodrug compound to the subject. Using a prodrug compound can be advantageous in maintaining a sustained blood concentration of dexmedetomidine in the subject. The prodrug compound may be derived from dexmedetomidine or an isomer thereof. The prodrug compound is administered in an amount that achieves a blood concentration of dexmedetomidine, or a pharmaceutically acceptable salt thereof, in the subject in the range of 100 pg/mL to 2000 pg/mL.

Pharmaceutical Compositions of an Alpha-2A Adrenergic Agonist and an Alpha-1 Adrenergic Agonist The present disclosure further provides pharmaceutical compositions comprising an alpha-2A adrenergic agonist, or a pharmaceutically acceptable salt thereof, and an alpha-1 adrenergic agonist, or a pharmaceutically acceptable salt thereof. When administered to a human subject, the alpha-2A adrenergic agonist, or pharmaceutically acceptable salt thereof, crosses the subject's blood-brain barrier thereby acting upon the subject's central nervous system, whereas the alpha-1 adrenergic agonist does not cross the subject's blood-brain barrier. The alpha-1 adrenergic agonist minimizes or eliminates the negative systemic vascular effects induced by the alpha-2A adrenergic agonist that causes the negative cerebral autoregulatory response, thereby enabling the alpha-2A adrenergic agonist to increase glymphatic flow. In an example embodiment, the pharmaceutical composition comprises an amount of an alpha-2A adrenergic agonist, or a pharmaceutically acceptable salt thereof, and an amount of an alpha-1 adrenergic agonist, or a pharmaceutically acceptable salt thereof, that are effective for improving glymphatic flow in the brain of a subject. In another example embodiment, the pharmaceutical composition comprises an amount of an alpha-2A adrenergic agonist, or a pharmaceutically acceptable salt thereof, and an amount of an alpha-1 adrenergic agonist, or a pharmaceutically acceptable salt thereof, that are effective for treating neurodegenerative disease in a subject, including dementia, Alzheimer's disease, and Parkinson's disease.

In one aspect, the pharmaceutical composition may comprise an amount of an alpha-2A adrenergic agonist or pharmaceutically acceptable salt thereof that is in the range of 40 micrograms to 400 micrograms and an amount of an alpha-1 adrenergic agonist or pharmaceutically acceptable salt thereof that is in the range of 2 milligrams to 15 milligrams. In a further embodiment, the pharmaceutical composition may comprise an amount of an alpha-2A adrenergic agonist or pharmaceutically acceptable salt thereof that is in the range of 80 micrograms to 300 micrograms and an amount of an alpha-1 adrenergic agonist or pharmaceutically acceptable salt thereof that is in the range of 5 milligrams to 13 milligrams. In yet another embodiment, the pharmaceutical composition may comprise an amount of an alpha-2A adrenergic agonist or pharmaceutically acceptable salt thereof that is in the range of 100 micrograms to 200 micrograms and the amount of an alpha-1 adrenergic agonist or pharmaceutically acceptable salt thereof is in the range of 7 milligrams to 12 milligrams. In certain embodiments of the foregoing compositions, the alpha-2A adrenergic agonist or pharmaceutically acceptable salt thereof may exhibit a bioavailability of 10% to 100%, or 50% to 95%, or 50% to 90%. Similarly, in certain embodiments of the foregoing compositions, the alpha-1 adrenergic agonist or pharmaceutically acceptable salt thereof may exhibit a bioavailability of 50% to 99%, or 50% to 95%, or 50% to 90%.

In another aspect, the pharmaceutical composition may comprise an amount of an alpha-2A adrenergic agonist or pharmaceutically acceptable salt thereof that achieves a blood concentration in a subject in the range of 100 pg/mL to 2000 pg/mL and an amount of an alpha-1 adrenergic agonist or pharmaceutically acceptable salt thereof that achieves a blood concentration in the subject in the range of 5 ng/mL to 100 ng/mL. In a further embodiment, the pharmaceutical composition may comprise an amount of an alpha-2A adrenergic agonist or pharmaceutically acceptable salt thereof that achieves a blood concentration in a subject in the range of 150 pg/mL to 1500 pg/mL and an amount of an alpha-1 adrenergic agonist or pharmaceutically acceptable salt thereof that achieves a blood concentration in the subject in the range of 10 ng/ml to 75 ng/mL. In yet another embodiment, the pharmaceutical composition may comprise an amount of an alpha-2A adrenergic agonist or pharmaceutically acceptable salt thereof that achieves a blood concentration in a subject in the range of 200 pg/mL to 1000 pg/mL and an amount of an alpha-1 adrenergic agonist or pharmaceutically acceptable salt thereof that achieves a blood concentration in the subject in the range of 20 ng/mL to 50 ng/mL.

In another aspect wherein the pharmaceutical composition is administered through the gastrointestinal tract, the amounts of the alpha-2A adrenergic agonist and the alpha-1 adrenergic agonist in the composition are adjusted to compensate for differences in bioavailability of the alpha-2A adrenergic agonist and the alpha-1 adrenergic agonist to achieve the target therapeutic plasma levels that deliver the specified pharmacodynamic effect.

In any of the foregoing example pharmaceutical compositions comprising an alpha-2A adrenergic agonist, which crosses the blood-brain barrier, and the alpha-1 adrenergic agonist, which does not cross the blood brain barrier, both the alpha-2A adrenergic agonist and the alpha-1 adrenergic agonist have an elimination half-life of 2-3 hours in an adult human subject.

In any of the foregoing example pharmaceutical compositions comprising an alpha-2A adrenergic agonist and an alpha-1 adrenergic agonist, the alpha-2A adrenergic agonist and the alpha-1 adrenergic agonist have a similar time to reach maximum concentration in the blood ("T max") when administered orally to a human adult subject. More specifically the T max for the alpha-2A adrenergic agonist does not diverge by more than 20% from the T max for the alpha-1 adrenergic agonist.

In any of the foregoing example pharmaceutical compositions comprising an alpha-2A adrenergic agonist and an alpha-1 adrenergic agonist, the alpha-2A adrenergic agonist is selected from dexmedetomidine, tizanidine, and brimonidine. Dexmedetomidine, tizanidine, and brimonidine share common characteristics including an elimination half-life of 2-3 hours in an adult human subject and a selectivity for alpha-2A receptors relative to alpha-2B and alpha-2C receptors.

In any of the foregoing example pharmaceutical compositions comprising an alpha-2A adrenergic agonist and an alpha-1 adrenergic agonist, the alpha-1 adrenergic agonist is selected from midodrine and phenylephrine. Midodrine and phenylephrine share common characteristics including not crossing the blood-brain barrier and an elimination half-life of 2-3 hours in an adult human subject.

In any of the foregoing example pharmaceutical compositions comprising an alpha-2A adrenergic agonist and an alpha-1 adrenergic agonist, the pharmaceutical composition may further comprise one or more pharmaceutically acceptable carriers. As examples, the pharmaceutically acceptable carriers may be selected from the group consisting of a liposome, a polymer matrix, a sugar, a starch, cellulose, a wax, a polyol, a buffering agent, agar, and a saline solution.

In any of the foregoing example pharmaceutical compositions comprising an alpha-2A adrenergic agonist and an alpha-1 adrenergic agonist, the alpha-2A adrenergic agonist, or pharmaceutically acceptable salt thereof, and the alpha-1 adrenergic agonist, or pharmaceutically acceptable salt thereof, are provided as separate components of the pharmaceutical composition.

In any of the foregoing example pharmaceutical compositions comprising an alpha-2A adrenergic agonist and an alpha-1 adrenergic agonist, the alpha-2A adrenergic agonist, or pharmaceutically acceptable salt thereof, and the alpha-1 adrenergic agonist, or pharmaceutically acceptable salt thereof, are provided as integrated components of the pharmaceutical composition.

In any of the foregoing example pharmaceutical compositions comprising an alpha-2A adrenergic agonist and an alpha-1 adrenergic agonist, the pharmaceutical composition may be provided in a dosage form selected from the group consisting of a film, a wafer, a patch, a lozenge, a gel, a spray, a tablet, a capsule, a suppository, a powder, and a liquid drop.

In any of the foregoing example pharmaceutical compositions comprising an alpha-2A adrenergic agonist and an alpha-1 adrenergic agonist, the pharmaceutical composition may be formulated for oral, parenteral, or transmucosal administration.

In an alternative embodiment of any of the foregoing example pharmaceutical compositions, the pharmaceutical composition comprises an alpha-1 adrenergic agonist, or a pharmaceutically acceptable salt thereof; and, in place of the alpha-2A adrenergic agonist, the composition comprises a prodrug compound that achieves a blood concentration of the alpha-2A adrenergic agonist, or a pharmaceutically acceptable salt thereof, in a subject in the range of 100 pg/mL to 2000 pg/mL. Using a prodrug compound can be advantageous in maintaining a sustained blood concentration of the alpha-2A adrenergic agonist in the subject. The prodrug compound may be derived from dexmedetomidine or an isomer thereof. The alpha-1 agonist, or pharmaceutically acceptable salt thereof, may achieve a blood concentration in the subject in the range of 5 ng/mL to 100 ng/mL. Alternatively, the alpha-1 agonist, or pharmaceutically acceptable salt thereof, is present in the composition in the range of 2 milligrams to 15 milligrams.

In any of the foregoing example pharmaceutical compositions, the alpha-2A adrenergic agonist, or pharmaceutically acceptable salt thereof, and the alpha-1 adrenergic agonist, or pharmaceutically acceptable salt thereof, are present in an effective amount to treat one or more symptoms of a neurodegenerative disease, including dementia, Alzheimer's disease, and Parkinson's disease.

Formulations Comprising an Alpha-2A Adrenergic Agonist and an Alpha-1 Adrenergic Agonist The present disclosure provides formulations that deliver to a subject a therapeutically effective amount of an alpha-2A adrenergic agonist, or pharmaceutically acceptable salt thereof, and an alpha-1 adrenergic agonist, or pharmaceutically acceptable salt thereof. The formulations comprising the disclosed compositions may be formulated for oral, parenteral, or transmucosal administration. More specifically, the formulations comprising the disclosed compositions may have a dosage form selected from the group consisting of a film, a wafer, a patch, a lozenge, a gel, a spray, a tablet, a capsule, a suppository, a powder, and a liquid drop.

In one aspect, formulations comprising the disclosed compositions are administered parenterally to avoid degradation by the gastrointestinal tract. Such parenterally administered formulations may be administered by injection, and include, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection.

In another aspect, formulations comprising the disclosed compositions are administered transmucosally to avoid degradation by the gastrointestinal tract. Such transmucosally administered formulations may be administered through the oral mucosa, the sublingual mucosa, the buccal mucosa, the nasal mucosa, or the anal mucosa.

In yet another aspect, formulations comprising the disclosed compositions are administered through the gastrointestinal tract. Such formulations administered through the gastrointestinal tract may comprise an increased amount of the alpha-2A adrenergic agonist and the alpha-1 adrenergic agonist.

In one embodiment, a pharmaceutical formulation is provided that comprises an alpha-2A adrenergic agonist or a pharmaceutically acceptable salt thereof; an alpha-1 adrenergic agonist or a pharmaceutically acceptable salt thereof; and at least one pharmaceutically acceptable carrier or pharmaceutically acceptable excipient. In the foregoing embodiment, the pharmaceutically acceptable salt may be selected from hydrochloride, hydrobromide, sulphate, phosphate or acid phosphate, acetate, maleate, fumarate, lactate, tartrate, citrate and gluconate salt forms. In the foregoing embodiment, the pharmaceutically acceptable excipient may be selected from the group consisting of a diluent, a binder, a dye, a preservative, an antioxidant, a flavoring, and a lubricant. In the foregoing embodiment, the pharmaceutically acceptable carrier is selected from the group consisting of a liposome, a polymer matrix, a sugar, a starch, cellulose, a wax, a polyol, a buffering agent, agar, and a saline solution.

Methods of Treatment with an Alpha-2A Adrenergic Agonist and an Alpha-1 Adrenergic Agonist The present disclosure further provides methods of treatment with the foregoing compositions. The methods of treatment include administering to a human subject an effective amount of an alpha-2A adrenergic agonist, or a pharmaceutically acceptable salt thereof, and an effective amount of an alpha-1 adrenergic agonist, or a pharmaceutically acceptable salt thereof, for treating one or more symptoms of a neurodegenerative disease. The methods include administering an alpha-2A adrenergic agonist, or a pharmaceutically acceptable salt thereof, and an amount of an alpha-1 adrenergic agonist, or a pharmaceutically acceptable salt thereof, in any of the amounts provided in the previously described compositions. When administered to a human subject, the alpha-2A adrenergic agonist, or pharmaceutically acceptable salt thereof, crosses the subject's blood-brain barrier thereby acting upon the subject's central nervous system, whereas the alpha-1 adrenergic agonist does not cross the subject's blood-brain barrier. The alpha-1 adrenergic agonist minimizes or eliminates the negative systemic vascular effects induced by the alpha-2A adrenergic agonist that causes the negative cerebral autoregulatory response, thereby enabling the alpha-2A adrenergic agonist to increase glymphatic flow.

In an example embodiment, the method of treatment comprises administering an amount of an alpha-2A adrenergic agonist, or a pharmaceutically acceptable salt thereof, and an amount of an alpha-1 adrenergic agonist, or a pharmaceutically acceptable salt thereof, that are effective for improving glymphatic flow in the brain of a subject. In another example embodiment, the method of treatment comprises administering an amount of an alpha-2A adrenergic agonist, or a pharmaceutically acceptable salt thereof, and an amount of an alpha-1 adrenergic agonist, or a pharmaceutically acceptable salt thereof, that are effective for treating neurodegenerative disease in a subject, including dementia, Alzheimer's disease, and Parkinson's disease.

In one aspect, the method comprises administering an amount of an alpha-2A adrenergic agonist, or a pharmaceutically acceptable salt thereof, and an amount of an alpha-1 adrenergic agonist, or a pharmaceutically acceptable salt thereof, to the subject simultaneously.

In another aspect, the method comprises administering to the subject an amount of an alpha-2A adrenergic agonist, or a pharmaceutically acceptable salt thereof, before administering to the subject an amount of an alpha-1 adrenergic agonist, or a pharmaceutically acceptable salt thereof.

In yet another aspect, the method comprises administering to the subject an amount of an alpha-2A adrenergic agonist, or a pharmaceutically acceptable salt thereof, after administering to the subject an amount of an alpha-1 adrenergic agonist, or a pharmaceutically acceptable salt thereof.

In any of the foregoing methods of treatment, the alpha-2A adrenergic agonist and the alpha-1 adrenergic agonist both have an elimination half-life of 2-3 hours in an adult human subject.

In any of the foregoing methods of treatment, the alpha-2A adrenergic agonist crosses the blood-brain barrier and the alpha-1 adrenergic agonist does not cross the blood brain barrier, while both have a similar time to reach maximum concentration in the blood ("T max") when administered orally to a human adult subject. More specifically the T max for the alpha-2A adrenergic agonist does not diverge by more than 20% from the T max for the alpha-1 adrenergic agonist.

In any of the foregoing methods of treatment, the alpha-2A adrenergic agonist is selected from dexmedetomidine, tizanidine, and brimonidine. Dexmedetomidine, tizanidine, and brimonidine share common characteristics including an elimination half-life of 2-3 hours in an adult human subject and a selectivity for alpha-2A receptors relative to alpha-2B and alpha-2C receptors.

In any of the foregoing methods of treatment, the alpha-1 adrenergic agonist is selected from midodrine and phenylephrine. Midodrine and phenylephrine share common characteristics including not crossing the blood-brain barrier and an elimination half-life of 2-3 hours in an adult human subject.

In any of the foregoing methods of treatment, the method may further comprise administering the alpha-2A adrenergic agonist, or pharmaceutically acceptable salt thereof, and/or the alpha-1 adrenergic agonist, or pharmaceutically acceptable salt thereof, with one or more pharmaceutically acceptable carriers. As examples, the pharmaceutically acceptable carriers may be selected from the group consisting of a liposome, a polymer matrix, a sugar, a starch, cellulose, a wax, a polyol, a buffering agent, agar, and a saline solution.

In any of the foregoing example methods, the alpha-2A adrenergic agonist, or pharmaceutically acceptable salt thereof, and the alpha-1 adrenergic agonist, or pharmaceutically acceptable salt thereof, are administered as separate components of a pharmaceutical composition.

In any of the foregoing example methods, the alpha-2A adrenergic agonist, or pharmaceutically acceptable salt thereof, and the alpha-1 adrenergic agonist, or pharmaceutically acceptable salt thereof, are administered as integrated components of the pharmaceutical composition.

In any of the foregoing example methods, the alpha-2A adrenergic agonist, or pharmaceutically acceptable salt thereof, and the alpha-1 adrenergic agonist, or pharmaceutically acceptable salt thereof, may be provided in a dosage form selected from the group consisting of a film, a wafer, a patch, a lozenge, a gel, a spray, a tablet, a capsule, a suppository, a powder, and a liquid drop.

In any of the foregoing example methods, the alpha-2A adrenergic agonist, or pharmaceutically acceptable salt thereof, and the alpha-1 adrenergic agonist, or pharmaceutically acceptable salt thereof, may be formulated for oral, parenteral, or transmucosal administration.

In an alternative embodiment of any of the foregoing example methods, in place of administering the alpha-2A adrenergic agonist, the effective amount of alpha-2A adrenergic agonist is achieved by administration of a prodrug compound to the subject. Using a prodrug compound can be advantageous in maintaining a sustained blood concentration of the alpha-2A adrenergic agonist in the subject. The prodrug compound may be derived from the alpha-2A adrenergic agonist or an isomer thereof. The prodrug compound is administered in an amount that achieves a blood concentration of the alpha-2A adrenergic agonist, or a pharmaceutically acceptable salt thereof, in the subject in the range of 100 pg/mL to 2000 pg/mL.

Definitions

The following definitions are provided to further elucidate the disclosure. These definitions should be read as would be understood by a person of ordinary skill in the art.

Transitional phrases such as "comprising," "including," "carrying," "having," "containing," "involving," "holding," "associated," "associated with," and the like are to be understood to be open-ended and to mean including but not limited to.

"Pharmaceutically acceptable salt(s)" refers to salts of acidic or basic groups that may be present in compounds used in the present compositions.

"Pharmaceutically acceptable carrier" refers to a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the formulation and not injurious to the patient.

A "subject" or a "patient" refers to any mammal (e.g., a human), such as a mammal that may be susceptible to a disease or disorder, for example, diabetes. In various embodiments, a subject refers to one that has been or will be the object of treatment, observation, or experiment.

"Treat," "treatment" or "treating" refers to an amelioration of a disease or disorder, or at least one sign or symptom thereof. In another embodiment, "treatment" or "treating" refers to an amelioration of at least one measurable physical parameter, not necessarily discernible by the patient. In yet another embodiment, "treatment" or "treating" refers to reducing the progression of a disease or disorder, for example, by reducing the rate of disease progression compared to a reference population having the same disease or decreasing the degree or rate or progression of a sign or symptom in the subject prior to treatment. In yet another embodiment, "treatment" or "treating" refers to delaying the onset of a disease or disorder, e.g., compared to a reference population or other method of determining such a parameter as is known by those in the art.

"Therapeutically effective amount" means that amount of therapeutic effective agent that is effective for producing a desired therapeutic effect. Accordingly, a therapeutically effective amount treats or prevents a disease or a disorder, or ameliorates at least one sign or symptom of the disorder.

"Therapeutic effect" refers to a local or systemic effect in animals, particularly mammals, and more particularly humans caused by a pharmacologically active substance.

"Oral administration" refers to treatment of a disease or disorder by delivery of therapeutically effective agents through the mouth. The agent may permeate through the oral mucosa or anywhere throughout the gastrointestinal tract. Oral administration includes, but is not limited to, solid dosage forms such as tablet, chewable tablet, lozenge, powder, dissolving film, gum, as well as homogenous and heterogeneous liquids, including emulsions.

"Systemic administration," "administered systemically," "peripheral administration" and "administered peripherally" refer to the administration of a composition, therapeutic or other material other than directly into the central nervous system, such that it enters the patient's system and, thus, is subject to metabolism and other like processes, for example, intravenous, subcutaneous, or oral administration.

"Parenteral administration" and "administered parenterally" refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection.

What is claimed:

1. An orally or parenterally administered pharmaceutical composition comprising
    dexmedetomidine, or a pharmaceutically acceptable salt thereof; and
    midodrine, or a pharmaceutically acceptable salt thereof.

2. The orally or parenterally administered pharmaceutical composition of claim 1, wherein the dexmedetomidine, or the pharmaceutically acceptable salt thereof, is 240 micrograms to 2400 micrograms and the midodrine, or the pharmaceutically acceptable salt thereof, is 2 milligrams to 15 milligrams.

3. The orally or parenterally administered pharmaceutical composition of claim 1, wherein the dexmedetomidine, or the pharmaceutically acceptable salt thereof, is present in an effective amount to achieve a maximum blood concentration in a subject of 100 pg/mL to 2000 pg/mL and the midodrine, or the pharmaceutically acceptable salt thereof, is present in an effective amount to achieve a maximum blood concentration of active metabolite desglymidodrine in the subject of 5 ng/mL to 100 ng/mL.

4. The orally or parenterally administered pharmaceutical composition according to claim 1, wherein the pharmaceutical composition further comprises one or more pharmaceutically acceptable carriers.

5. The orally or parenterally administered pharmaceutical composition according to claim 1, wherein the dexmedetomidine, or the pharmaceutically acceptable salt thereof, and the midodrine, or the pharmaceutically acceptable salt thereof, are provided as separate components of the pharmaceutical composition.

6. The orally or parenterally administered pharmaceutical composition according to claim 1, wherein the dexmedetomidine, or the pharmaceutically acceptable salt thereof, and the midodrine, or the pharmaceutically acceptable salt thereof, are provided as integrated components of the pharmaceutical composition.

7. The orally or parenterally administered pharmaceutical composition according to claim 1, wherein the pharmaceutical composition is provided orally in a dosage form selected from the group consisting of a film, a wafer, a lozenge, a gel, a spray, a tablet, a capsule, a powder, and a liquid drop.

8. The orally or parenterally administered pharmaceutical composition according to claim 1, wherein the dexmedetomidine, or the pharmaceutically acceptable salt thereof, and the midodrine, or the pharmaceutically acceptable salt thereof, are present in an effective amount to enhance clearance of proteinopathy proteins in a human.

9. A method comprising orally or parenterally administering a pharmaceutical composition to a human, the pharmaceutical composition comprising dexmedetomidine, or a pharmaceutically acceptable salt thereof, and midodrine, or a pharmaceutically acceptable salt thereof.

10. The method according to claim 9, wherein the dexmedetomidine, or the pharmaceutically acceptable salt thereof, and the midodrine, or the pharmaceutically acceptable salt thereof, are administered to the subject simultaneously.

11. The method according to claim 9, wherein the midodrine, or the pharmaceutically acceptable salt thereof, is administered to the human before the dexmedetomidine, or the pharmaceutically acceptable salt thereof, is administered to the human.

12. The method according to claim 9, wherein the dexmedetomidine, or the pharmaceutically acceptable salt thereof, that is administered is 240 micrograms to 2,400 micrograms, and the midodrine, or the pharmaceutically acceptable salt thereof, that is administered is 2 milligrams to 15 milligrams.

13. The method according to claim 9, wherein the dexmedetomidine, or the pharmaceutically acceptable salt thereof, that is administered achieves a maximum blood concentration in the human of 100 pg/mL to 2000 pg/mL and the midodrine, or the pharmaceutically acceptable salt thereof, that is administered achieves a maximum blood concentration of active metabolite desglymidodrine in the human of 5 ng/ml to 100 ng/mL.

14. The method according to claim 9, wherein the dexmedetomidine, or the pharmaceutically acceptable salt thereof, and the midodrine, or the pharmaceutically acceptable salt thereof, are administered as separate components of a pharmaceutical composition.

15. The method according to claim 9, wherein the dexmedetomidine, or the pharmaceutically acceptable salt thereof, and the midodrine, or the pharmaceutically acceptable salt thereof, are administered as integrated components of a pharmaceutical composition.

16. The method according to claim 9, wherein the pharmaceutical composition is provided orally in a dosage form selected from the group consisting of a film, a wafer, a lozenge, a gel, a spray, a tablet, a capsule, a powder, and a liquid drop.

17. An orally or parenterally administered pharmaceutical formulation comprising dexmedetomidine or a pharmaceutically acceptable salt thereof;

midodrine or a pharmaceutically acceptable salt thereof; and at least one pharmaceutically acceptable carrier or pharmaceutically acceptable excipient.

18. The orally or parenterally administered pharmaceutical formulation according to claim 17, wherein the pharmaceutically acceptable salt is selected from hydrochloride, hydrobromide, sulphate, phosphate or acid phosphate, acetate, maleate, fumarate, lactate, tartrate, citrate and gluconate salt forms.

19. The orally or parenterally administered pharmaceutical formulation according to claim 17, wherein the pharmaceutically acceptable excipient is selected from the group consisting of a diluent, a binder, a dye, a preservative, an antioxidant, a flavoring, and a lubricant.

20. The orally or parenterally administered pharmaceutical formulation according to claim 17, wherein the pharmaceutically acceptable carrier is selected from the group consisting of a liposome, a polymer matrix, a sugar, a starch, cellulose, a wax, a polyol, a buffering agent, agar, and a saline solution.

21. The orally or parenterally administered pharmaceutical formulation according to claim 17, wherein the pharmaceutical formulation is provided orally and in a dosage form selected from the group consisting of a film, a wafer, a lozenge, a gel, a spray, a tablet, a capsule, a powder, and a liquid drop.

22. The orally or parenterally administered pharmaceutical formulation according to claim 17, wherein the dexmedetomidine, or the pharmaceutically acceptable salt thereof, and the midodrine, or the pharmaceutically acceptable salt thereof, are present in an effective amount to enhance clearance of proteinopathy proteins in a human.

23. The orally or parenterally administered pharmaceutical formulation according to claim 17, wherein the pharmaceutical formulation is administered orally, and wherein the dexmedetomidine, or the pharmaceutically acceptable salt thereof, is 240 micrograms to 2400 micrograms and the midodrine, or the pharmaceutically acceptable salt thereof, is 2 milligrams to 15 milligrams.

24. The orally or parenterally administered pharmaceutical formulation according to claim 17, wherein the dexmedetomidine, or the pharmaceutically acceptable salt thereof, is present in an effective amount to achieve a maximum blood concentration in a subject of 100 pg/mL to 2000 pg/mL and the midodrine, or the pharmaceutically acceptable salt thereof, is present in an effective amount to achieve a maximum blood concentration of active metabolite desglymidodrine in the subject of 5 ng/ml to 100 ng/mL.

25. The orally or parenterally administered pharmaceutical formulation according to claim 17, wherein the dexmedetomidine, or the pharmaceutically acceptable salt thereof, achieves a maximum blood concentration in a subject of 100 pg/mL to 2000 pg/mL at a T max-d time interval and the midodrine, or the pharmaceutically acceptable salt thereof, achieves a maximum blood concentration of active metabolite desglymidodrine in the subject of 5 ng/mL to 100 ng/mL at a T max-m time interval, wherein the T max-d time interval does not diverge from the T-max-m time interval by more than 20%.

26. The orally or parenterally administered pharmaceutical composition of claim 1, wherein the dexmedetomidine, or the pharmaceutically acceptable salt thereof, achieves a maximum blood concentration in a subject of 100 pg/mL to 2000 pg/mL at a T max-d time interval and the midodrine, or the pharmaceutically acceptable salt thereof, achieves a maximum blood concentration of active metabolite desglymidodrine in the subject of 5 ng/ml to 100 ng/ml at a T max-m time interval, wherein the T max-d time interval does not diverge from the T-max-m time interval by more than 20%.

27. The method of claim 9, wherein the dexmedetomidine, or the pharmaceutically acceptable salt thereof, achieves a maximum blood concentration in the human of 100 pg/mL to 2000 pg/mL at a T max-d time interval and the midodrine, or the pharmaceutically acceptable salt thereof, achieves a maximum blood concentration of active metabolite desglymidodrine in the human of 5 ng/mL to 100 ng/mL at a T max-m time interval, wherein the T max-d time interval does not diverge from the T-max-m time interval by more than 20%.

28. The method of claim 9, wherein the dexmedetomidine, or the pharmaceutically acceptable salt thereof, and the midodrine, or the pharmaceutically acceptable salt thereof, are present in an effective amount to enhance clearance of proteinopathy proteins in the human.

29. The orally or parenterally administered pharmaceutical composition of claim 1, wherein the dexmedetomidine, or the pharmaceutically acceptable salt thereof, is 40 to 400 micrograms and the midodrine, or the pharmaceutically acceptable salt thereof, is 2 milligrams to 15 milligrams.

30. The method of claim 9, wherein the dexmedetomidine, or the pharmaceutically acceptable salt thereof, that is administered is 40 to 400 micrograms, and the midodrine, or the pharmaceutically acceptable salt thereof, that is administered is 2 milligrams to 15 milligrams.

\* \* \* \* \*